(12) United States Patent
Weir

(10) Patent No.: US 8,050,520 B2
(45) Date of Patent: Nov. 1, 2011

(54) METHOD FOR CREATING A PIXEL IMAGE FROM SAMPLED DATA OF A SCANNED BEAM IMAGER

(75) Inventor: Michael P. Weir, Blanchester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 888 days.

(21) Appl. No.: 12/056,710

(22) Filed: Mar. 27, 2008

(65) Prior Publication Data

US 2009/0245599 A1 Oct. 1, 2009

(51) Int. Cl.
*G06K 9/36* (2006.01)

(52) U.S. Cl. ........ 382/289; 382/296; 359/214.1; 359/215.1; 359/220.1; 359/221.1; 359/225.1; 359/226.1; 359/226.2

(58) Field of Classification Search .......... 359/214.1, 359/215.1, 220.1, 221.1, 225.1, 226.1, 226.2; 382/289, 296
See application file for complete search history.

(56) References Cited

U.S. PATENT DOCUMENTS

| | | |
|---|---|---|
| 3,758,199 A | 9/1973 | Thaxter |
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |
| 4,643,967 A | 2/1987 | Bryant |
| 4,676,231 A | 6/1987 | Hisazumi et al. |
| 4,760,840 A | 8/1988 | Fournier, Jr. et al. |
| 4,803,550 A | 2/1989 | Yabe et al. |
| 4,872,458 A | 10/1989 | Kanehira et al. |
| 4,902,083 A | 2/1990 | Wells |
| 4,902,115 A | 2/1990 | Takahashi |
| 4,934,773 A | 6/1990 | Becker |

(Continued)

FOREIGN PATENT DOCUMENTS

DE 3837248 5/1990

(Continued)

OTHER PUBLICATIONS

Linda Shapiro and George Stockman, Computer Vision, Prentice Hall 2001.*

(Continued)

*Primary Examiner* — Wesley Tucker
*Assistant Examiner* — Mark Roz

(57) ABSTRACT

A method for creating a pixel image in a two-dimensional display coordinate system from sampled data derived from a collector of a scanned beam imager adapted to transmit a beam of radiation which traces a trajectory in a two-dimensional acquisition coordinate system. The trajectory contains datum locations in the acquisition coordinate system associated with the sampled data. The method includes receiving the sampled data. The method also includes adjusting a mathematical model of the trajectory based on a function of at least one of rotation, translation, and desired scaling of the model of the trajectory. The method also includes constructing the pixel image in the display coordinate system from the adjusted model of the trajectory.

7 Claims, 7 Drawing Sheets

U.S. PATENT DOCUMENTS

| | | |
|---|---|---|
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,436,655 A | 7/1995 | Hiyama et al. |
| 5,467,104 A | 11/1995 | Furness, III et al. |
| 5,488,862 A | 2/1996 | Neukermans et al. |
| 5,519,198 A * | 5/1996 | Plesko ................... 235/462.4 |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 | 4/2001 | Lai |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |

| Patent | Date | Inventor |
|---|---|---|
| 6,462,770 B1 | 10/2002 | Cline et al. |
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B1 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 | 2/2004 | Kilcoyne et al. |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,795,221 B1 | 9/2004 | Urey |
| 6,802,809 B2 | 10/2004 | Okada |
| 6,803,561 B2 | 10/2004 | Dunfield |
| 6,821,245 B2 | 11/2004 | Cline et al. |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel et al. |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,271,383 B2 | 9/2007 | Chee |
| 7,391,013 B2 | 6/2008 | Johnston et al. |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 | 8/2002 | Waner et al. |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |
| 2003/0159447 A1 | 8/2003 | Sergio et al. |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1 | 1/2005 | Ishihara et al. |
| 2005/0020926 A1 | 1/2005 | Wiklof et al. |
| 2005/0023356 A1 | 2/2005 | Wiklof et al. |
| 2005/0030305 A1 | 2/2005 | Brown et al. |

| | | | |
|---|---|---|---|
| 2005/0038322 A1 | 2/2005 | Banik | |
| 2005/0116038 A1 | 6/2005 | Lewis et al. | |
| 2005/0162762 A1 | 7/2005 | Novak | |
| 2005/0187441 A1 | 8/2005 | Kawasaki et al. | |
| 2005/0203343 A1 | 9/2005 | Kang et al. | |
| 2005/0240147 A1 | 10/2005 | Makower et al. | |
| 2006/0010985 A1 | 1/2006 | Schneider | |
| 2006/0084867 A1 | 4/2006 | Tremblay et al. | |
| 2006/0164330 A1 | 7/2006 | Bright et al. | |
| 2006/0183246 A1 | 8/2006 | Wiesner et al. | |
| 2006/0195014 A1 | 8/2006 | Seibel et al. | |
| 2006/0238774 A1 | 10/2006 | Lindner et al. | |
| 2006/0245971 A1 | 11/2006 | Burns et al. | |
| 2006/0284790 A1 | 12/2006 | Tegreene et al. | |
| 2007/0038119 A1 | 2/2007 | Chen et al. | |
| 2007/0046778 A1 | 3/2007 | Ishihara et al. | |
| 2007/0135770 A1 | 6/2007 | Hunt et al. | |
| 2007/0156021 A1 | 7/2007 | Morse et al. | |
| 2007/0161876 A1 | 7/2007 | Bambot et al. | |
| 2007/0162093 A1 | 7/2007 | Porter et al. | |
| 2007/0167681 A1 | 7/2007 | Gill et al. | |
| 2007/0173707 A1 | 7/2007 | Mitra | |
| 2007/0179366 A1 | 8/2007 | Pewzner et al. | |
| 2007/0197874 A1 | 8/2007 | Ishihara | |
| 2007/0197875 A1 | 8/2007 | Osaka | |
| 2007/0203413 A1 | 8/2007 | Frangioni | |
| 2007/0213588 A1 | 9/2007 | Morishita et al. | |
| 2007/0213618 A1 | 9/2007 | Li et al. | |
| 2007/0225695 A1 | 9/2007 | Mayer et al. | |
| 2007/0238930 A1 | 10/2007 | Wiklof et al. | |
| 2007/0244365 A1 | 10/2007 | Wiklof | |
| 2007/0260121 A1 | 11/2007 | Bakos et al. | |
| 2007/0260273 A1 | 11/2007 | Cropper et al. | |
| 2008/0058629 A1 | 3/2008 | Seibel et al. | |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | 98/13720 | 4/1998 |
| WO | 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | 2006/049787 | 5/2006 |
| WO | 2006/055733 | 5/2006 |
| WO | 2007/041542 | 4/2007 |
| WO | 2007/067163 | 6/2007 |
| WO | 2007/070831 | 6/2007 |
| WO | 2007/084915 | 7/2007 |

OTHER PUBLICATIONS

Invitation to Pay Additional Fees with Partial International Search Report, PCT/US2008/074275 (Jan. 16, 2009).
Invitation to Pay Additional Fees with Partial International Search Report, PCT/US2008/074273 (Dec. 30, 2008).
Kiang, M-H et al., "Surface-Micromachined Electrostatic-Comb Driven Scanning Micromirrors for Barcode Scanners" (date of first publication unknown).
Lewis, J.R. et al., "Scanned beam medical imager," MOEMS Display and Imaging Systems II, Proceedings of SPIE vol. 5348, pp. 40-51 (2004).
James, R. et al., "Update on MEMS-based Scanned Beam Imager" (date of first publication unknown).
Wiklof, C., "Display technology spawns laser camera," Laser Focus World (Dec. 2004).
"Press Information—Phillips' Fluid Lenses Bring Things into Focus," http://www.newscenter.philips.com (Mar. 3, 2004).
Lettice, J., "The $5 'no moving parts' fluid zoom lens—twice," The Register (Mar. 15, 2004).
"Volcano Products—IVUS Imaging Visions® PV018," http://www.volcanotherapeutics.com (date of first publication unknown).
Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).
"Crystalplex Technology—PlxBead™ Superior Qualities," http:www.crystalplex.com (date of first publication unknown).
"Microvision [illuminating information] Products/Overview, Corporate Overview Presentation 2006".
"Holographic Beam Combiner for Ladar, Printer, Fiber Optics, and Cancer Treatment," by Digital Optics Technologies, Inc., http://www.mdatechnology.net (date of first publication unknown).
Brown, D.M., Abstract from SPIE Digital Library for "High-power laser diode beam combiner," Optical Engineering, vol. 42, Issue 11 (2003).
Literature entitled "All fiber beam combiner from Point Source" (Oct. 13, 2006).
"Custom Polarizing Cube Beamsplitters," from GlobalSpec The Engineering Search Engine, http://www.globalspec.com (date of first publication unknown).
Literature entitled "Dallas Semiconductor MAXIM—Visible-Laser Driver has Digitally Controlled Power Modulation," Maxim Integrated Products, http://www.maxim-ic.com (Jul. 1, 2001).
"SCAN Mode Strategies for SCUBA-2" (May 25, 2005).
Seifert, M. et al., "High Power Diode Laser Beam Scanning in Multi-Kilowatt Range," Proceedings of the 23rd International Congress on Applications of Lasers and Electro-Optics (2004).
Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).
"Bladeless Trocars," by Johnson http://wvvw.jnjgateway.com (date of first publication unknown).
Yeh, R. et al., "Microelectromechanical Components for Articulated Microrobots" (date of first publication unknown).
Xu, Q. et al., "Micrometre-scale silicon electro-optic modulator," Nature, vol. 435, pp. 325-327 (May 19, 2005).
Park, H. et al., "Development of Double-Sided Silicon Strip Position Sensor," 2005 IEEE Nuclear Science Symposium Conference Record, pp. 781-785 (2005).
Hammond, S.W., "Architecture and Operation of a Systolic Sparse Matrix Engine," Proceedings of the 3rd SIAM Conference on Parallel Processing for Scientific Computing, pp. 419-423 (1987).
Ra, H. et al., "Biomedical Optics & Medical Imaging—Microtechnology enables endoscopic confocal microscopy," SPIE (http://spie.org) (2007).
International Search Report issued regarding International Application No. PCT/US2007/078868 (Mar. 28, 2008).
PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
PCT, International Search Report, PCT/US2008/066552 (Oct. 23, 2008).

* cited by examiner

METHOD FOR CREATING A PIXEL IMAGE FROM SAMPLED DATA OF A SCANNED BEAM IMAGER

FIELD OF THE INVENTION

The present invention is related generally to scanned beam systems, and more particularly to a method for creating a pixel image from sampled data of a scanned beam imager.

BACKGROUND OF THE INVENTION

Conventional scanned light beam systems, such as those adapted to function as bar code scanners, are available from Microvision, Inc. of Redmond, Wash.

An example of an endoscope application of a medical scanned laser beam imager is given in US Patent Application Publication 2005/0020926. The scanned laser beam imager includes a two-dimensional MEMS (micro-electromechanical system) scanner. The MEMS scanner is a dual-resonant-mirror scanner. The mirror scanner scans, about substantially orthogonal first and second axes, one or more light beams (such as light beams from red, green and blue lasers) through an optical dome at high speed in a pattern that traces a trajectory in a two-dimensional acquisition coordinate system. The scanned laser beam imager uses at least one light detector in creating a pixel image from the reflected light for display on a monitor.

Direct view and camera type endoscopes and laparoscopes are known which are "angled scopes" having a direction of view which is not parallel to the central longitudinal axis of the insertion tube of the instrument.

Software programs sold with digital cameras are known which can rotate a pixel image displayed on a computer monitor wherein the pixel image was uploaded to the computer from the digital camera.

What is needed is an improved method for creating a pixel image from sampled data of a scanned beam imager.

SUMMARY

A first method of the invention is for creating a pixel image in a two-dimensional rectangular display coordinate system from sampled data derived from a collector of a scanned beam imager having an oscillating reflector. The reflector has a surface and has substantially orthogonal first and second axes of rotation. The reflector oscillates in a resonant mode about the first and second axes of rotation causing a beam of radiation reflected from the surface to trace a substantially Lissajous trajectory in a two-dimensional acquisition coordinate system. The Lissajous trajectory contains datum locations in the acquisition coordinate system associated with the sampled data. The reflector has a third axis of rotation substantially orthogonal to the first and second axes of rotation of the reflector. The first method includes receiving the sampled data. The first method also includes derotating a mathematical model of the Lissajous trajectory to account for rotation of the scanned beam imager about the third axis of rotation from a reference orientation. The first method also includes constructing the pixel image in the display coordinate system from the derotated model. The first method also includes displaying the constructed pixel image.

A second method of the invention is for creating a pixel image in a two-dimensional display coordinate system from sampled data derived from a collector of a scanned beam imager adapted to transmit a beam of radiation which traces a trajectory in a two-dimensional acquisition coordinate system. The trajectory contains datum locations in the acquisition coordinate system associated with the sampled data. Rotation of the scanned beam imager about an imager axis causes rotation of the trajectory in the acquisition coordinate system. The second method includes receiving the sampled data. The second method also includes derotating a mathematical model of the trajectory to account for the rotation of the scanned beam imager about the imager axis from a reference orientation. The second method also includes constructing the pixel image in the display coordinate system from the derotated model. The second method also includes performing at least one of storing the constructed pixel image in a memory and displaying the constructed pixel image.

A third method of the invention is for creating a pixel image in a two-dimensional display coordinate system from sampled data derived from a collector of a scanned beam imager adapted to transmit a beam of radiation which traces a trajectory in a two-dimensional acquisition coordinate system. The trajectory contains datum locations in the acquisition coordinate system associated with the sampled data. The third method includes receiving the sampled data. The third method also includes adjusting a mathematical model of the trajectory based on a function of at least one rotation, translation, and desired scaling of the model. The third method also includes constructing the pixel image in the display coordinate system from the adjusted model. The third method also includes performing at least one of storing the constructed pixel image in a memory and displaying the constructed pixel image.

Several benefits and advantages are obtained from one or more or all of the methods of the invention. In one example of the first method, derotating the model of the trajectory instead of derotating a constructed pixel image should save in power consumption and hardware complexity. In one example of the second method, the two-dimensional display coordinate system is other than a two-dimensional rectangular display coordinate system and the scanned beam imager does not have a reflector which oscillates in a resonant mode about substantially orthogonal first and second axes of rotation. In one example of the third method, the adjusted model of the trajectory increases or lessens or accounts for rotation and translation of the model of the trajectory due to rotation and translation of the scanned beam imager from a reference orientation and location, and the adjusted model of the trajectory zooms in on or out from the non-scaled model of the trajectory.

DETAILED DESCRIPTION

Before explaining several methods of the present invention in detail, it should be noted that each is not limited in its application or use to the details of construction and arrangement of parts and steps illustrated in the accompanying drawings and description. The illustrative methods of the invention may be implemented or incorporated in other methods, variations and modifications, and may be practiced or carried out in various ways. Furthermore, unless otherwise indicated, the terms and expressions employed herein have been chosen for the purpose of describing the illustrative methods of the present invention for the convenience of the reader and are not for the purpose of limiting the invention.

It is further understood that any one or more of the following-described methods and enablements, applications, etc. thereof can be combined with any one or more of the other following-described methods and enablements, applications, etc. thereof.

U.S. patent application Ser. No. 11/716,806, entitled MEDICAL DEVICE INCLUDING SCANNED BEAM UNIT FOR IMAGING AND THERAPY, and filed Mar. 12, 2007, is incorporated by reference as if fully set forth herein.

Figure 1:
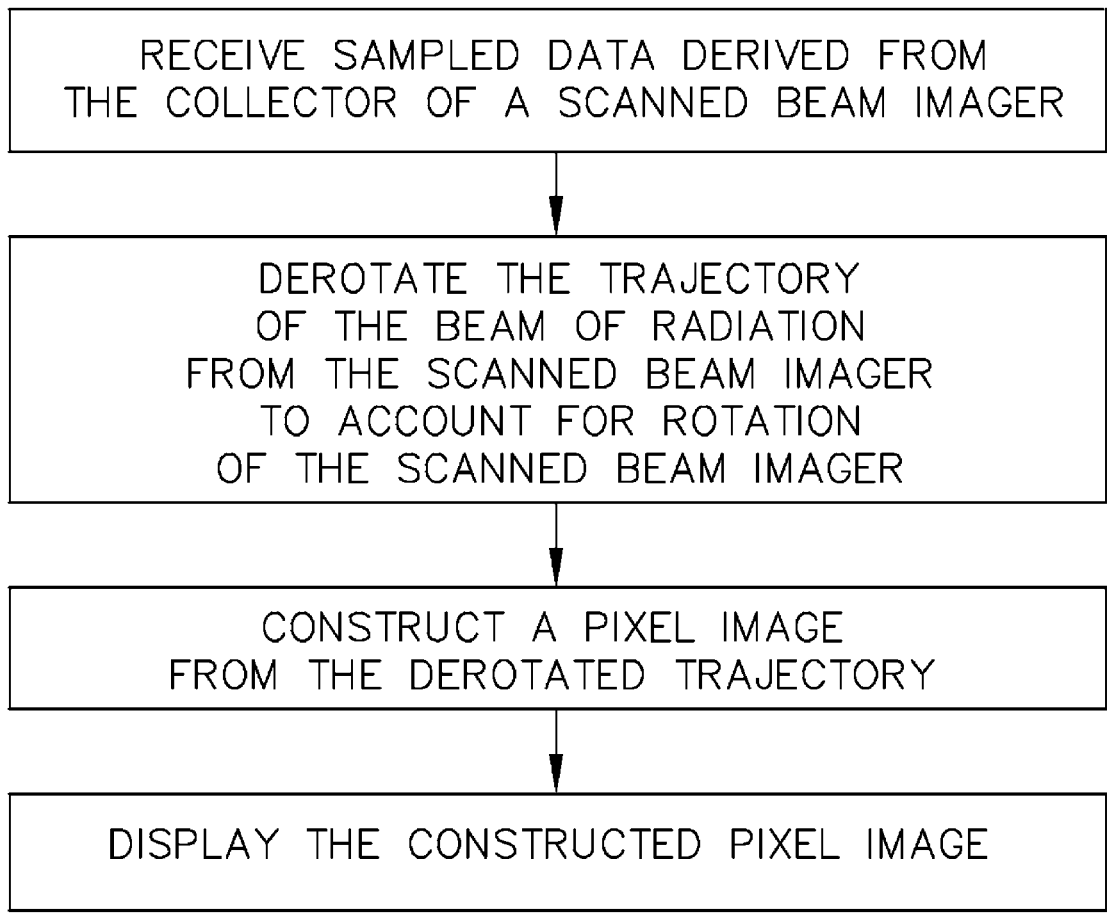
FIG. 1 is a block diagram of the first method of the invention.
Figure 2:
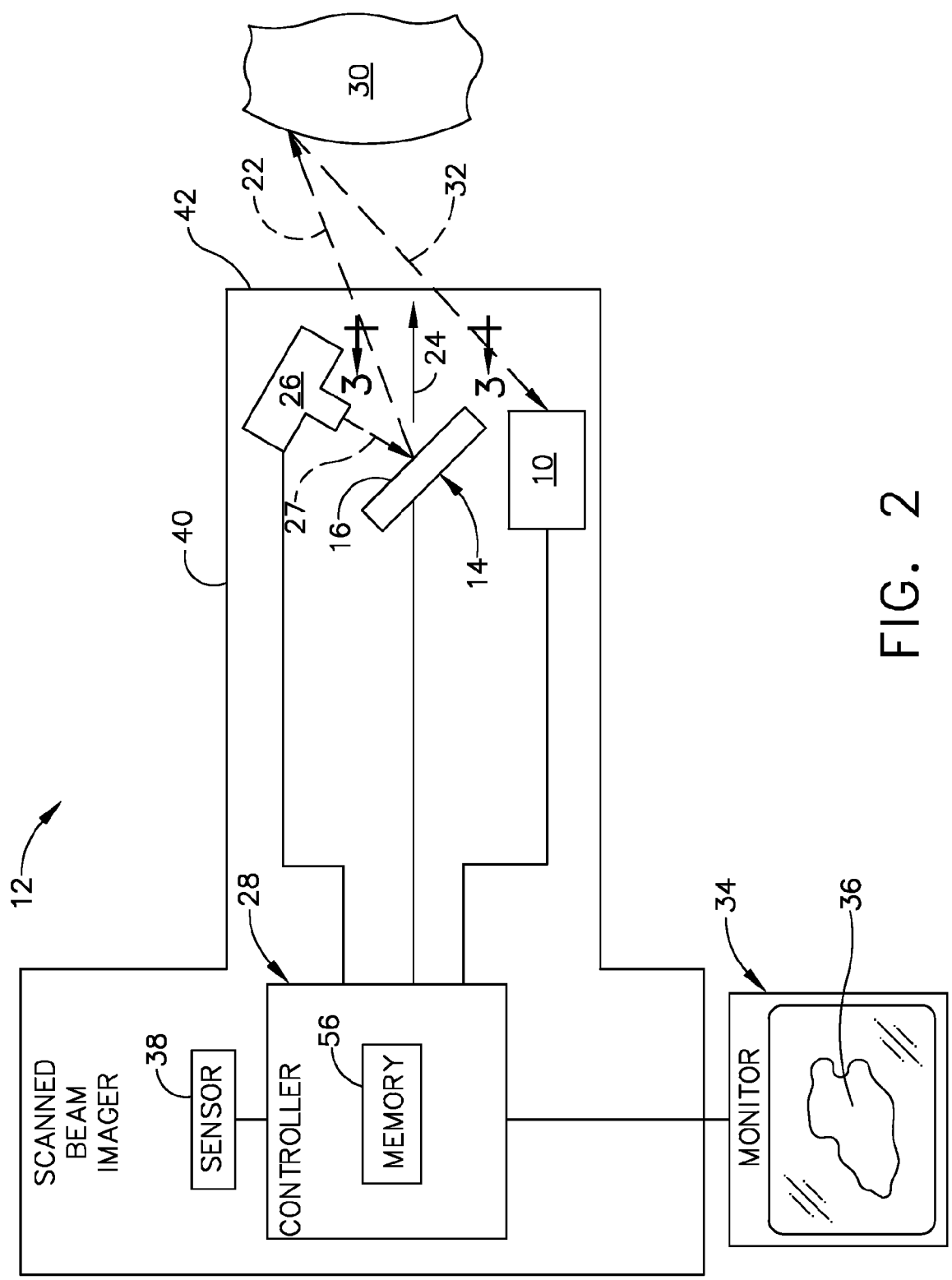
FIG. 2 is a schematic diagram of an embodiment of a monitor and a scanned beam imager including a reflector and a collector which can be used in performing the first method of FIG. 1, wherein the central longitudinal axis of the imager is substantially parallel to the third axis of rotation of the reflector.
Figure 3:
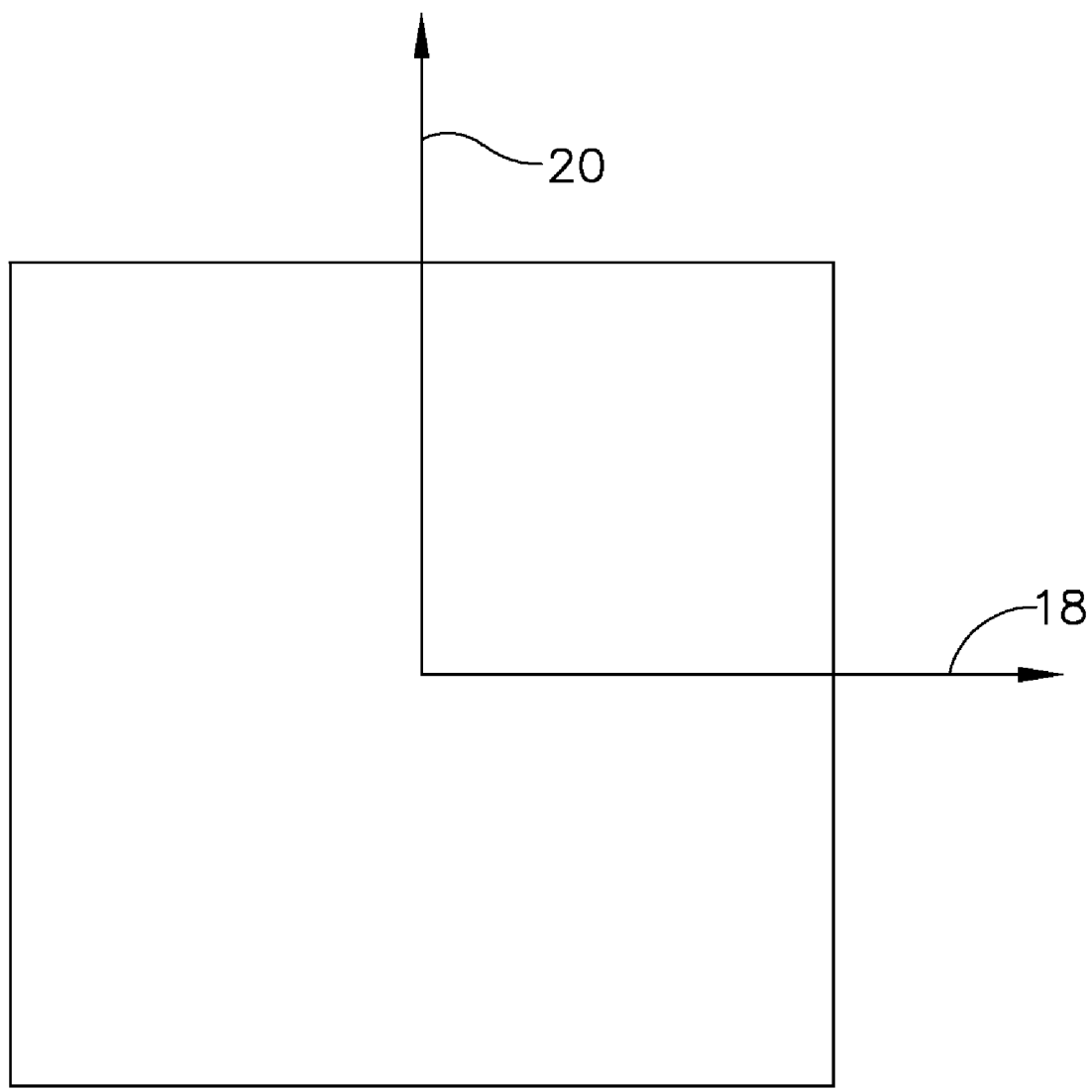
FIG. 3 is a view of the reflector of FIG. 2 taken along lines 3-3 of FIG. 2 and showing the first and second axes of rotation of the reflector.

Referring now to the drawings, wherein like numerals represent like elements throughout, a first method of the invention is shown in FIG. 1 and an example of an embodiment for carrying out the first method is shown in FIGS. 2-3. The first method is for creating a pixel image in a two-dimensional rectangular display coordinate system from sampled data derived from a collector 10 of a scanned beam imager 12 having an oscillating reflector 14. The reflector 14 has a surface 16 and has substantially orthogonal first and second axes of rotation 18 and 20 (seen in FIG. 3). The reflector 14 oscillates in a resonant mode about the first and second axes of rotation causing a beam of radiation 22 reflected from the surface 16 to trace a substantially Lissajous trajectory in a two-dimensional acquisition coordinate system. The Lissajous trajectory contains datum locations in the acquisition coordinate system associated with the sampled data. The reflector 14 has a third axis of rotation 24 (seen in FIG. 2) substantially orthogonal to the first and second axes of rotation 18 and 20 of the reflector 14. The first method includes receiving the sampled data. The first method also includes derotating a mathematical model of the Lissajous trajectory to account for rotation of the scanned beam imager 12 about the third axis 24 from a reference orientation. The first method also includes constructing the pixel image in the display coordinate system from the derotated model. The first method also includes displaying the constructed pixel image. It is pointed out that the derotating is done in the acquisition coordinate system.

In the example of the embodiment of FIGS. 2-3, the scanned beam imager 12 includes a radiation beam source assembly 26 (such as, but not limited to, a laser assembly) adapted to emit a radiation beam 27 (such as, but not limited to, a light beam) toward the surface 16 of the reflector 14 and includes a controller 28 which is operatively connected to the reflector 14, to the radiation beam source assembly 26, and to the collector 10. The beam of radiation 22 from the reflector 14 strikes a location on a target 30, and returned radiation 32 is received by the collector 10. In the example, the collector 10 also acts as a radiation detector and takes data samples of the returned radiation 32 and sends the data samples to the controller 28. Other arrangements for receiving the sampled data are left to the artisan. In the example, the controller 28 derotates the model and constructs the pixel image from the derotated model, wherein the controller 28 is operatively connected to a monitor 34 to display the constructed pixel image as a displayed image 36.

In one employment of the first method, the reference orientation is a user-inputted upright viewing position. In one variation, the first method also includes inserting at least a portion of the scanned beam imager 12 into a patient wherein the portion includes the reflector 14 and the collector 10. In one modification, the scanned beam imager 12 is inserted by a user through a first trocar into the abdomen of a patient, an operating surgeon performing laparoscopic surgery on the patient directs the user to rotate the scanned beam imager 12 until the displayed image 36 on the monitor 34 is in an upright viewing position, and the user inputs the upright viewing position by pushing a button on the scanned beam imager which directs the controller 28 to consider this position to be the reference orientation.

In one enablement of the first method, the sampled data is sampled at a constant sampling rate. In one variation, each sampled datum of the derotated model in the acquisition coordinate system is distributed into proximate pixel locations in the display coordinate system. In one modification, the distribution is in accord with a weighting function which decreases monotonically with distance between a particular datum location of the derotated model and each proximate pixel location associated with the particular datum location of the derotated model. In one illustration, only pixel locations within a predetermined distance from the particular datum location of the derotated model are considered to be proximate pixel locations associated with the particular datum location of the derotated model.

In one application of the first method, the rotation of the scanned beam imager 12 from the reference orientation is derived from at least one output of at least one sensor 38 affixed to the scanned beam imager 12. In the same or a different application, the scanned beam imager 12 has an insertion tube 40 which is insertable into a patient, and the reflector 14 and the collector 10 are disposed within the insertion tube 40 proximate a distal end 42 of the insertion tube 40.

In one arrangement involving the first method, the scanned beam imager 12 is a "straight scope" wherein the insertion tube 14 when straight has a central longitudinal axis which is substantially coaxially aligned with the third axis of rotation 24 of the reflector 14. In a different arrangement, as seen in the scanned beam imager 112 of FIG. 4, the scanned beam imager 112 is an "angled scope" wherein the insertion tube 140 when straight has a central longitudinal axis 44 which is not substantially orthogonal to a plane defined by the first and second axes of rotation 18 and 20 of the reflector 14. In this different arrangement, the controller 28 transforms the rotation angle of the insertion tube 40 into a rotation angle of the third axis 24 of rotation of the reflector 14. In one variation, the insertion tube of the "straight scope" and/or the "angled scope" is flexible. In a different variation, the insertion tube of the "straight scope" and/or the "angled scope" is rigid.

A detailed explanation of one implementation of the first method is given in the following paragraphs.

The scanned beam imager 12 employs an oscillating reflector 14 with substantially orthogonal first and second axes of rotation 18 and 20. The reflector 14 oscillates in a resonant mode about the first and second axes of rotation 18 and 20. The rate of oscillation is typically higher in one axis than the other. When properly excited, the oscillating reflector 14 causes a beam of radiation 22 reflected from its surface 16 to trace a Lissajous trajectory in a two-dimensional acquisition coordinate system. Only a portion of a mathematical model 46 of the Lissajous trajectory, including datum locations 48 of the sampled data, is shown in the two-dimensional acquisition coordinate system of FIG. 5. The coordinates (x',y') of the model 46 in the two-dimensional acquisition coordinate system as shown in FIG. 5 are approximated by $$x'(t)=A\sin(w_f t+\phi_f)$$

$$y'(t)=B\cos(w_s t+\phi_s).$$

Figure 5:
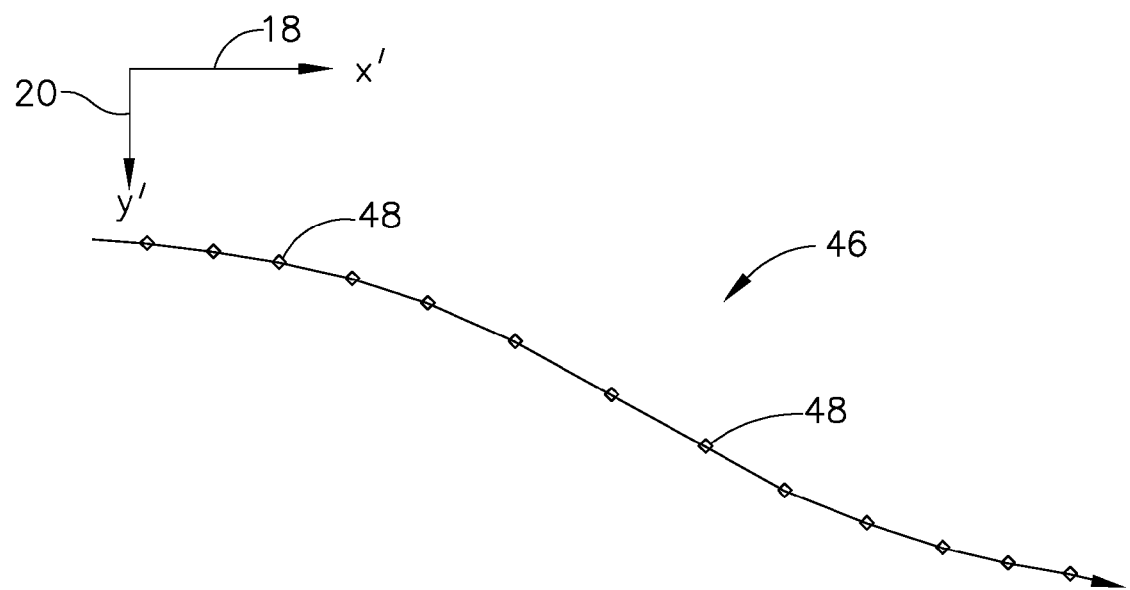
FIG. 5 is an illustration of a two-dimensional acquisition coordinate system with an example of a portion of a mathematical model of a rotated Lissajous trajectory including datum locations associated with sampled data from the collector of FIG. 2, wherein the rotation of the model of the trajectory was caused by the scanned beam imager having been rotated by a user from an upright viewing position.

However, because the scanned beam imager 12 was rotated by a user causing the reflector 14 to be rotated about the third axis of rotation 24 of the reflector 14 by an angle λ from a user-inputted upright viewing position, the model 46 of FIG. 5 is a rotated model. The controller 28 determines the angle λ from the at-least-one output of the at-least-one sensor 38 and the known geometry of the reflector and the at-least-one sensor 38.

Figure 6:
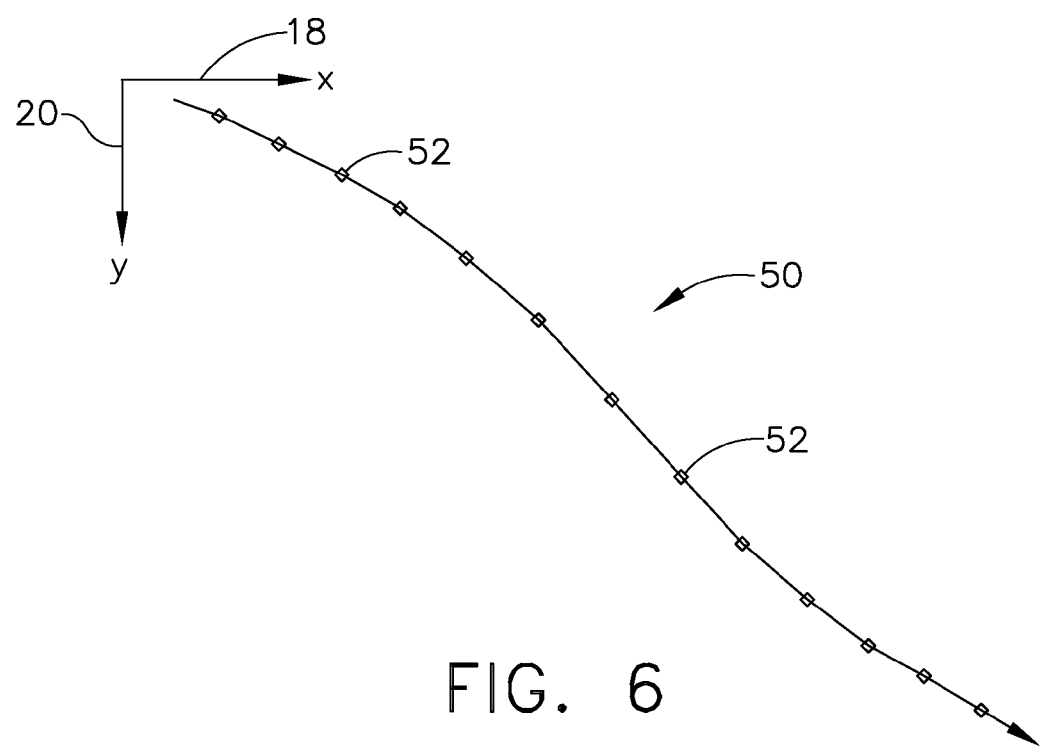
FIG. 6 is an illustration, as in FIG. 5, but of an example of a portion of the derotated model of the trajectory which accounts for the rotation of the model of the trajectory in FIG. 5, wherein the portion shown in FIG. 5 and the portion shown in FIG. 6 represent the same portion of a Lissajous figure, one rotated with respect to the other.

The controller 28 derotates the rotated model 46 to account for (i.e., to substantially totally cancel out the effects of) rotation of the scanned beam imager 12 about the third axis of rotation 24 of the reflector 14 from the user-inputted upright viewing position. The derotated model 50 includes datum locations 52 of the sampled data. The coordinates (x,y) of the derotated model 50 in the two-dimensional acquisition coordinate system as shown in FIG. 6 are $$x(t)=x'(t)\cos\lambda - y'(t)\sin\lambda$$

$$y(t)=y'(t)\cos\lambda + x'(t)\sin\lambda.$$

Based on the phase relationship of the slow (s) and fast (f) axis motion, the derotated model 50 of the basic Lissajous pattern can precess. The number of slow axis cycles required to precess the pattern to an initial spatial point, is called the interleave factor.

The Lissajous pattern is spatially repeated after a set number of oscillations on the slow axis (interleave factor). Once a reference point on the derotated model 50 of the complete set of Lissajous patterns is identified, one can view the constant sample time, digital data stream captured by the collector 10 as a vector of constant length, the Scanned Data Vector $SDV_i$. The number N of samples in the vector $SDV_i$ is equal to the interleave factor times the period of the slow axis oscillation divided by the sample interval (Δt). The index i identifies the optical detector associated with the N samples. For example, i=R when the optical detector detects the color red.

$$SDV_i(j\Delta t)=[s(i,j)]_{j=0}^{N-1}.$$

If there are multiple optical detectors sampled coincidentally, then the scanned-beam-imager data stream can be viewed as a matrix, the Scanned Data Matrix (SDM), that has a row count equal to the number of sampled detectors (M) and a column count equal to the number N of samples in each $SDV_i$. In a system having three color (r—red, g—green, b—blue) plus fluorescence (f) channels, $$SDM = \begin{bmatrix} SDV_R \\ SDV_G \\ SDV_B \\ SDV_F \end{bmatrix}.$$

The pixel data matrix (PDM) is a two-dimensional matrix with row and column indices that represent the display space. In the above-described scanned beam imager 12, for example, there may be 600 rows (Y) and 800 columns (X) and each point in the data set may be a triple representing red (R), green (G), and blue (B) display intensities.

$$PDM = \begin{bmatrix} (r_{0,0}, g_{0,0}, b_{0,0}) & \cdots & (r_{0,799}, g_{0,799}, b_{0,799}) \\ \vdots & & \vdots \\ (r_{599,0}, g_{599,0}, b_{599,0}) & & (r_{599,799}, g_{599,799}, b_{599,799}) \end{bmatrix}.$$

In order to conveniently describe matrix operations, it may be useful to define a view of the matrix, PDM, that is a vector of length XY called PDV. The transformation between the two is not a matrix operation, but rather a reordering where the rows of PDM are constructed of successive blocks of PDV. Note that it is essential that the same reordering be used when accessing the PDV and the transformation matrix, T to be described next.

Figure 7:
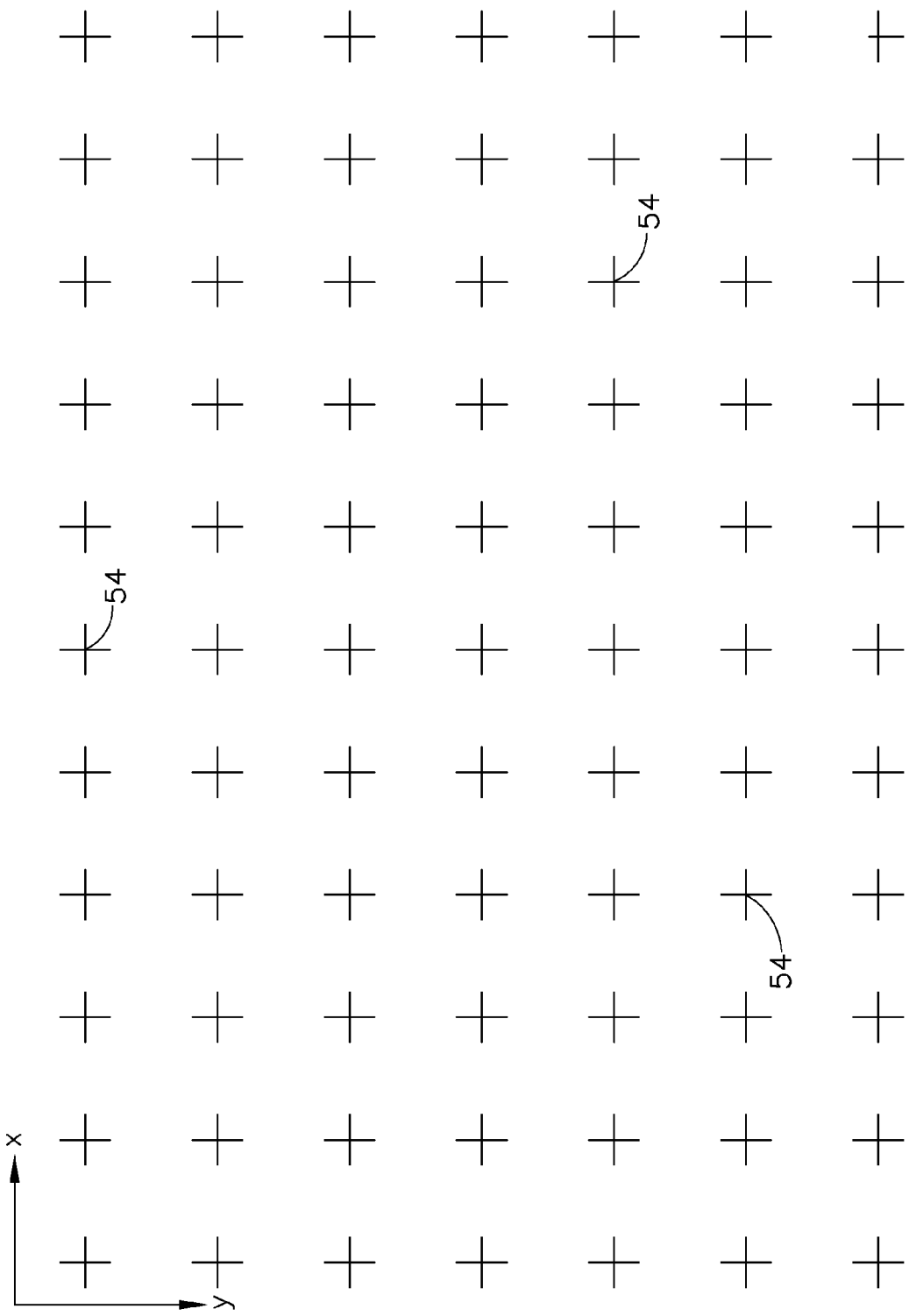
FIG. 7 is an illustration of an example of a portion of pixel locations in a two-dimensional rectangular display coordinate system used to construct a pixel image from the scanned beam imager of FIG. 2 and to display the constructed pixel image on the monitor of FIG. 2.

One exemplary method for transforming between acquisition and display space involves multiplication by a matrix T or its inverse. The process for constructing this matrix is given in a later section. Matrix T is an N row by XY column matrix where N is the number of samples in the SDV; X is the number of pixel columns in the display space; and Y is the number of pixel rows in the display space. FIG. 7 shows the pixel locations 54 in a two-dimensional rectangular display coordinate system.

Figure 8:
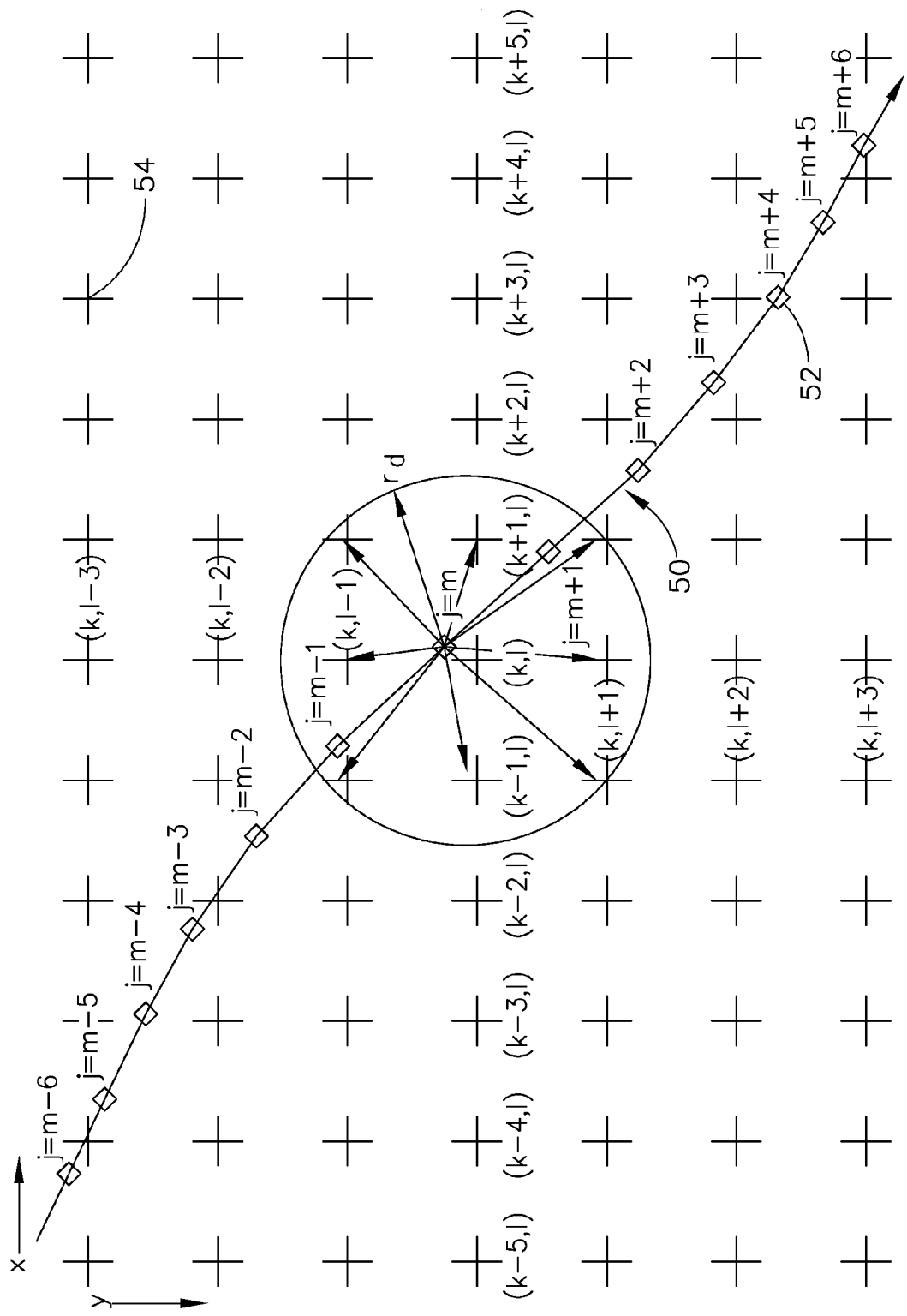
FIG. 8 is an illustration of overlaying the derotated model of the trajectory of FIG. 6 on FIG. 7.

When converting from the acquisition to display space, it may be helpful to take a close look at the physical situation from which the data derives. FIG. 8, which overlays the derotated model 50 of FIG. 6 onto FIG. 7, provides the basis for the following discussion.

In FIG. 8, the derotated model 50 is shown overlaying the pixel locations 54. The index into the data samples is j and the pixels have indices (k,l), corresponding to discrete values of conventional orthogonal Cartesian coordinates (x,y): not matrix indices (row, column). The origin of the pixel locations 54 is in the upper left hand corner. A sampled datum value from a particular datum location 52 will be distributed into pixels having pixel locations 54 falling into a region of radius $r_d$ centered on the particular datum location 52.

The solid line in FIG. 8 represents a portion of a derotated model 50 of the Lissajous trajectory of the beam of radiation 22. The diamonds indicate datum locations 52 along the derotated model 50. The sample index (j) increases from the top left to bottom right in this depiction. The trajectory of the beam of radiation 22 (with increasing sample index) in the derotated model 50 can be in any direction. Note that the samples at the top left and bottom right are closer together than the samples in the center of the figure. This difference is shown to reinforce the implications of a constant data-sampling rate applied to resonant scanned beams. The particular sample index on the beam, m, will be utilized in subsequent discussions.

Conversion from the acquisition space to the display space can be represented as a matrix multiplication, followed by a data reordering

[SDV][T]=[PDV]

where the pixel data vector PDV is then reordered to yield the pixel data matrix PDM. If the number of samples in the SDV vector is N and the size of the display space is X pixel columns by Y pixel rows, the transformation matrix, T, is of dimension N by (X*Y).

The following process can be used to populate the T matrix. Through precise knowledge of the path of the scanned beam of radiation 22 in the model 46 (that knowledge is assumed to be inherent in the scanner drive and positioning system, not shown, of the scanned beam imager 12) and hence in the derotated model 50, it is possible to identify the pixel location closest to the sample, m, at t=mΔt from the start of a frame. Denote that pixel with the indices (k,l). Next, construct a circle of radius, $r_d$, over which the sampled datum, m, is going to be distributed. Where s is zero or a positive or negative integer and t is zero, or a positive or negative integer, for each pixel (k+s,l+t) having a pixel location 54 within the constructed circle: (a) compute the length, l, of the vector from the datum location 52 of the sampled datum, m, to the center (pixel location 54) of the pixel (k+s,l+t); and (b) calculate a weighting value, w, that is proportional to the length, of the vector. Many functions can be used such as a function which decreases monotonically with distance, such as, for example:

$$w = e^{-F\frac{s}{r_d}}$$

where:
w is the weighting factor,
s is the length of the vector from the datum location to the pixel of interest
F is a controllable constant that sets how fast the effects of the sampled datum falls off as the value of l increases.
$r_d$ is the radius of the circle over which the sampled datum is being distributed.

Record the value of w into the transformation matrix T at the x,y location of the subject pixel (k+s,l+t). The location in the matrix will be at row m and column [(l+t)−1]*(X−1)+(k+s). It is noted that (l+t) is the row number of the subject pixel, X is the number of pixel columns in the display space, and (k+s) is the column number of the subject pixel. It should be recognized that this method creates a sparse matrix, T. To improve computational efficiency, one may optionally use various methods to create a banded matrix amenable to hardware acceleration or optimized software algorithms, such as described by Hammond S, Dunki-Jacobs R, Hardy R, Topka T. "Architecture and Operation of a Systolic Sparse Matrix Engine", Proceedings of the Third SIAM Conference on Parallel Processing for Scientific Computing, 1987, (419-423), the details of which are hereby incorporated by reference as if fully set forth herein.

A second method of the invention is for creating a pixel image in a two-dimensional display coordinate system from sampled data derived from a collector 10 of a scanned beam imager 12 adapted to transmit a beam of radiation 22 which traces a trajectory in a two-dimensional acquisition coordinate system The trajectory contains datum locations in the acquisition coordinate system associated with the sampled data. Rotation of the scanned beam imager 12 about an imager axis causes rotation of the trajectory in the acquisition coordinate system. The second method includes receiving the sampled data. The second method also includes derotating a mathematical model of the trajectory to account for the rotation of the scanned beam imager 12 about the imager axis from a reference orientation. The second method also includes constructing the pixel image in the display coordinate system from the derotated model. The second method also includes performing at least one of storing the constructed pixel image in a memory 56 and displaying the constructed pixel image. It is pointed out that the derotating is done in the acquisition coordinate system.

It is noted that the second method broadens the first method such as by covering a two-dimensional display coordinate system other than a two-dimensional rectangular display coordinate system and/or by using a scanned beam imager not having a reflector which oscillates in a resonant mode about substantially orthogonal first and second axes of rotation, etc. One of ordinary skill in the art, following the methodology described for the first method can modify the calculations of the first method to account for the broader coverage of the second method without undue experimentation.

In one employment of the second method, the reference orientation is a user-inputted upright viewing position. In one variation, the second method also includes inserting at least a portion of the scanned beam imager 12 into a patient wherein the portion includes the collector 10.

In one enablement of the second method, the sampled data is sampled at a constant sampling rate. In one variation, each sampled datum in the acquisition coordinate system is distributed into proximate pixel locations in the display coordinate system. In one modification, the distribution is in accord with a weighting function. In one illustration, only pixel locations within a predetermined distance from the particular datum location are considered to be proximate pixel locations associated with the particular datum location.

In one application of the second method, the rotation of the scanned beam imager 12 from the upright viewing position is derived from at least one output of at least one sensor 38 affixed to the scanned beam imager 12. In one modification, the scanned beam imager 12 has an insertion tube 40 which is insertable into a patient, and the collector 10 is disposed within the insertion tube 40 proximate a distal end 42 of the insertion tube 40. In one variation, as seen in an alternate embodiment of the scanned beam imager 112 in FIG. 4, the scanned beam imager 112 is an "angled scope" wherein the insertion tube 140 when straight has a central longitudinal axis 44 which is not substantially orthogonal to a plane defined by the two-dimensional acquisition coordinate system.

A third method of the invention is for creating a pixel image in a two-dimensional display coordinate system from sampled data derived from a collector 10 of a scanned beam imager 12 adapted to transmit a beam of radiation 22 which traces a trajectory in a two-dimensional acquisition coordinate system. The trajectory contains datum locations in the two-dimensional acquisition coordinate system associated with the sampled data. The third method includes receiving the sampled data. The third method also includes adjusting a mathematical model of the trajectory based on a function of at least one of rotation, translation, and desired scaling of the model. The third method also includes constructing the pixel image in the two-dimensional display coordinate system from the adjusted model. The third method also includes performing at least one of storing the constructed pixel image in a memory 56 and displaying the constructed pixel image. It is pointed out that the adjusting is done in the acquisition coordinate system.

It is noted that the third method broadens the second method such as covering rotation, translation, and/or desired scaling of the model of the trajectory, wherein, for example, the adjusted model of the trajectory may increase or lessen or account for rotation and translation of the model of the trajectory due to rotation and translation of the scanned beam imager from a reference orientation and location, and wherein, for example, the adjusted model of the trajectory may zoom in on or out from the non-scaled model of the trajectory. One of ordinary skill in the art, following the methodology described for the second method can modify the calculations of the second method to account for the broader coverage of the third method without undue experimentation. It is also noted that the employments, enablements, applications, etc. of the second method are equally applicable to the third method. In one variation, the translation is derived from at least one output of the at-least-one sensor 38. In one modification, the user inputs the desired scaling to the controller 28 using a touch screen window (not shown) on the monitor 34.

Figure 4:
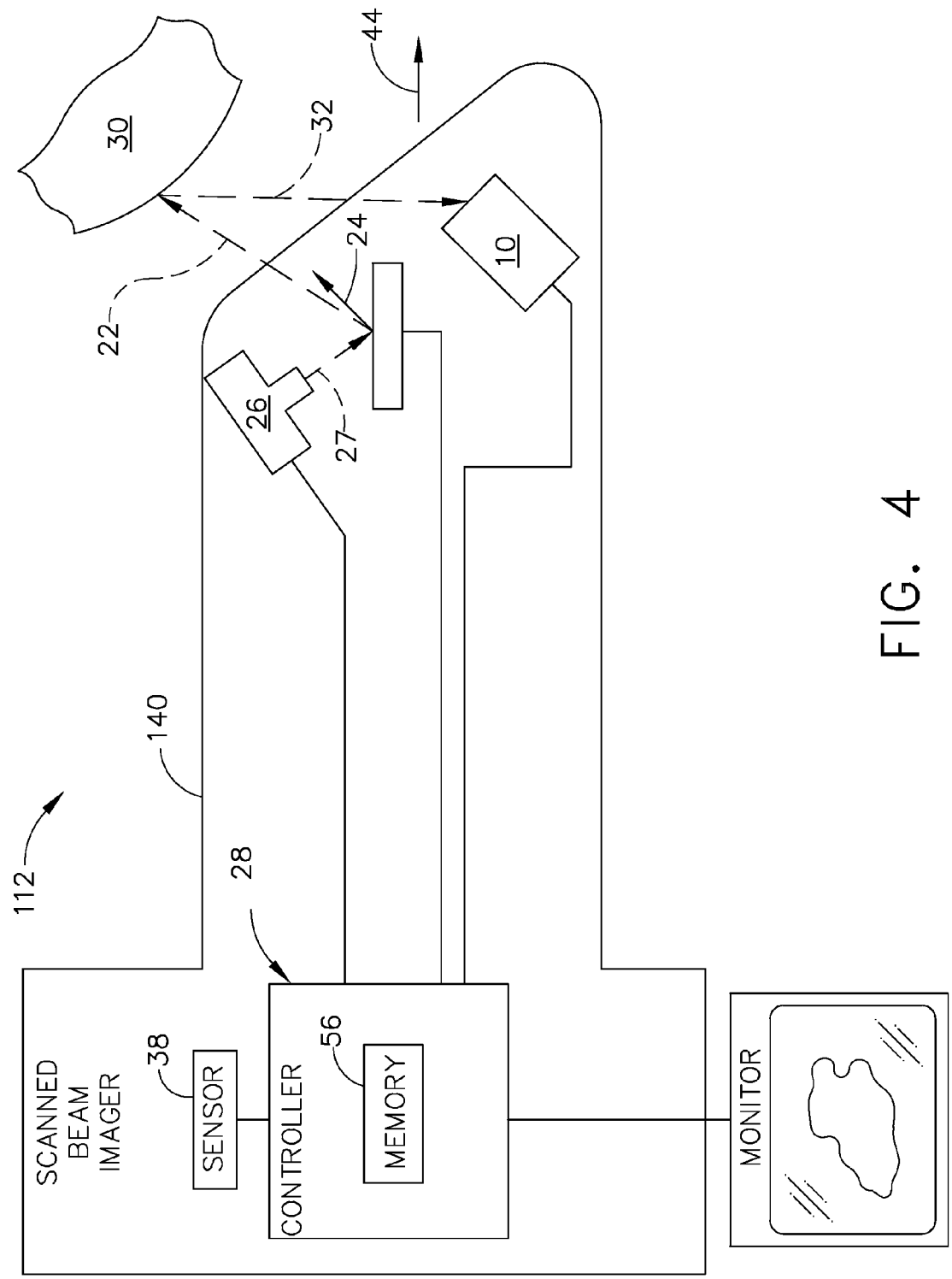
FIG. 4 is a view, as in FIG. 2, but showing an alternate embodiment of a scanned beam imager in the form of an "angled scope", wherein the central longitudinal axis of the imager is not substantially orthogonal to the first and second axes of rotation of the reflector.

In one extension of any one or more or all of the methods of the invention, the scanned beam imager 12 is adapted to have the radiation beam source assembly 26 emit a medical imaging radiation beam and a medical therapy radiation beam, wherein "therapy" means treatment of a medical condition. In one variation, the controller 28 is adapted to have the monitor 34 display the displayed image 36 whether or not the radiation beam 26 is a light beam. Examples of light beams include laser light beams and non-laser light beams. Examples of radiation beams, other than light beams, are left to those skilled in the art. It is noted that the unlabeled solid lines between components in FIGS. 2 and 4 represent connections between the components. It is also noted that the components of the scanned beam imager 12 may or may not be disposed within a single housing.

While the present invention has been illustrated by a description of several methods, it is not the intention of the applicant to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A method for creating a pixel image in a two-dimensional rectangular display coordinate system from sampled data derived from a collector of a scanned beam imager having an oscillating reflector, wherein the reflector has a surface, wherein the reflector has substantially orthogonal first and second axes of rotation, wherein the reflector oscillates in a resonant mode about the first and second axes of rotation causing a beam of radiation reflected from the surface to trace a substantially Lissajous trajectory in a two-dimensional acquisition coordinate system, wherein the Lissajous trajectory contains datum locations in the acquisition coordinate system associated with the sampled data, wherein the reflector has a third axis of rotation substantially orthogonal to the first and second axes of rotation of the reflector, and wherein the method comprises:
   a) receiving the sampled data;
   b) derotating a mathematical model of the Lissajous trajectory to account for rotation of the scanned beam imager about the third axis of rotation from a reference orientation;
   c) constructing the pixel image in the display coordinate system from the derotated model; and
   d) displaying the constructed pixel image.

2. The method of claim 1, wherein the reference orientation is a user-inputted upright viewing position.

3. The method of claim 2, also including inserting at least a portion of the scanned beam imager into a patient wherein the portion includes the reflector and the collector.

4. The method of claim 1, wherein the sampled data is sampled at a constant sampling rate.

5. The method of claim 1, wherein the rotation of the scanned beam imager from the reference orientation is derived from at least one output of at least one sensor affixed to the scanned beam imager.

6. The method of claim 1, wherein the scanned beam imager has an insertion tube which is insertable into a patient, and wherein the reflector and the collector are disposed within the insertion tube proximate a distal end of the insertion tube.

7. The method of claim 6, wherein the insertion tube when straight has a central longitudinal axis which is not substantially orthogonal to a plane defined by the first and second axes of rotation of the reflector.

* * * * *